Dec. 8, 1959 H. C. SWIM Plant Pat. 1,885
ROSE PLANT
Filed Jan. 8, 1959
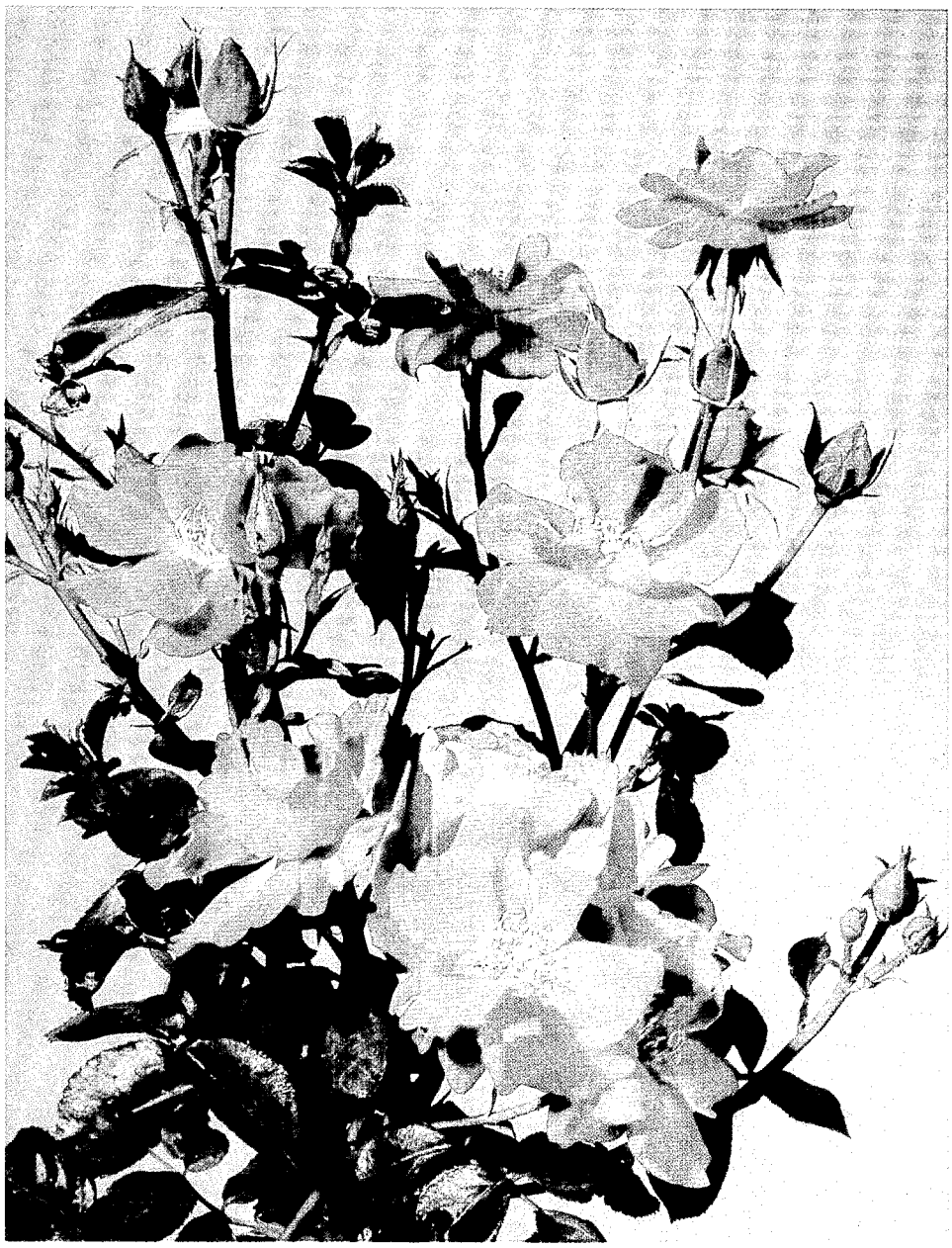
Inventor.
H. C. Swim
By: Robb & Robb
Attorneys.

United States Patent Office

Plant Pat. 1,885
Patented Dec. 8, 1959

1,885

ROSE PLANT

Herbert C. Swim, Ontario, Calif., assignor to Armstrong Nurseries, Inc., Ontario, Calif., a corporation of California Application January 8, 1959, Serial No. 785,771

1 Claim. (Cl. 47—61)

The present invention relates to a new and distinct variety of rose plant of the floribunda class, which was originated by me by crossing the variety "Gay Lady" (Plant Patent No. 719) with an unnamed and unpatented seedling also of the floribunda type and which was characterized by medium vigor and an upright-spreading habit, combined with a very floriferous habit and a habit of bearing very double orange-scarlet flowers of medium size, but in large clusters.

The general objective of this breeding was to produce a new rose variety with vigor, plant size and attractive, glossy foliage approaching those of the seed parent, "Gay Lady," combined with a flowering habit of the floribunda type approaching that of the unnamed pollen parent, and with a flower color in the range from red to orange-scarlet. This objective was fully achieved, as evidenced by the following unique combination of characteristics which are outstanding in the new variety and which distinguish it from its parents as well as from all other varieties of which I am aware:

(1) A very vigorous, bushy, upright-spreading plant habit;

(2) Attractive semi-glossy to glossy foliage of from medium to large size;

(3) Semi-double flowers of from small to medium size and borne in clusters of medium size; and (4) A bright, relatively unfading flower color ranging from Cherry to Rose Red.

In comparison with its seed parent, "Gay Lady," the new variety is more floriferous; it bears its flowers in medium sized clusters, as distinguished from the blooms of this parent which are mostly borne on single stems; and the flowers are of semi-double form, as distinguished from the double flowers of "Gay Lady."

As compared with its unnamed pollen parent, the new variety is much more vigorous; the flower clusters are smaller; the blooms are semi-double, as distinguished from the very double flowers of this parent; and the blooms are more red in color, as distinguished from the orange-scarlet color of this parent.

Asexual reproduction of the new variety by both cuttings and budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Bush; outdoor; seedling; for cut flowers and for garden decoration.

Class: Floribunda.

Breeding: Seedling.

*Seed parent.*—"Gay Lady."

*Pollen parent.*—An unnamed seedling.

Propagation: Holds its distinguishing characteristics through succeeding propagations by both cuttings and budding.

*Flower*

Locality where grown and observed: Ontario, California.

Flowers borne: Usually 3 to 5 or more to stem; in regular, rounded clusters; on strong, short stems.

Quantity of bloom: Very abundant, outdoors.

Continuity: Nearly continuous during growing season.

Fragrance: Slight.

Bud:

*Peduncle.*—From short to average length; average caliper; erect; moderately smooth; numerous stipitate glands extending on to base of receptacle. Color—near absinthe Green, Plate XXXI (Ridgway).

*Before calyx breaks.*—Size—small. Form—short; pointed; ovoid.

*As calyx breaks.*—Color—between Chrysanthemum Crimson, Plate 824/1, page 169 (Wilson) and Oxblood Red, Plate 00823/3, page 191 (Wilson).

*Sepals.*—Inner surface—with fine, woolly tomentum; margins of alternate sepals have stipitate glands and few slender, small, foliaceous appendages; margins of other sepals with tomentum only. Outer surface—moderately smooth; with few stipitate glands.

*As first petal opens.*—Size—small. Form—short; pointed; ovoid. Color: Outside—near Cardinal Red, Plate 822/2, page 168 (Wilson), with small area at base of petal near attachment near Primrose Yellow, Plate 601/2, page 65 (Wilson); Inside—near Currant Red, Plate 821/2, page 167 (Wilson), with small area at base of petal near attachment near Primrose Yellow, Plate 601/1, page 65 (Wilson).

*Opening.*—Opens up well; is not retarded from opening by cold, hot, wet or dry weather.

Bloom:

*Size (when fully open).*—From small to average; from 2½ inches to 3 inches.

*Petalage.*—Semi-double; from 10 to 14 petals, plus from 2 to 4 petaloids; arranged regularly.

*Form.*—High-centered at first, but becoming cupped; petals being at first somewhat loosely cupped, becoming later at maturity more loosely flat to cupped, with tips rolled outward.

Petals:

*Texture.*—From medium to thick; leathery. Inside—satiny. Outside—from slightly shiny to satiny.

*Shape.*—Outer—obovate, with apex usually flat and usually with 2 notches. Inside—obovote; somewhat irregular, with apex rounded and with 2 or 3 notches.

This description of a newly opened flower was made from a rose grown outdoors in the month of July at Ontario, California:

*Color.*—Outer petal: outside surface—near Rose Red, Plate 724/1, page 158 (Wilson), with small area at base of petal near attachment near Canary Yellow, Plate 2/3, page 2 (Wilson); inside surface—near Cherry, Plate 722, page 157 (Wilson), with small area at base near attachment near Canary Yellow, Plate 2/3, page 2 (Wilson). Inner petal: outside surface—near Rose Red, Plate 724/1, page 158 (Wilson), with small area at base of petal near attachment near Canary Yellow, Plate 2/3, page 2 (Wilson); inside surface—near Cherry, Plate 722, page 157 (Wilson), with small area at base near attachment near Canary Yellow, Plate 2/3, page 2 (Wilson).

This description was made from a rose that was open for 3 days outdoors in the month of July at Ontario, California:

*Color.*—Outer petal: outside surface—near Rose Red, Plate 724/3, page 158 (Wilson), with small area at base near attachment near Canary Yellow, Plate 2/3, page 2 (Wilson); inside surface—near Rose Red, Plate 724/1, page 158 (Wilson), with small area at base near attachment near Canary Yellow, Plate 2/3, page 2 (Wilson). Inner petal: outside surface—near Rose Red, Plate 724/3, page 158 (Wilson), with small area at base near attachment near Canary Yellow, Plate 2/3, page 2 (Wilson); inside surface—near Rose Red, Plate 724/1, page 158 (Wilson), with small area at base near attachment near Canary Yellow, Plate 2/3, page 2 (Wilson).

*General color effect.*—Newly opened flower—between Cherry, Plate 722/1, page 157 (Wilson) and Rose Red, Plate 724, page 158 (Wilson). 3-days open—between Cherry, Plate 722/2, page 157 (Wilson) and Rose Red, Plate 724/1, page 158 (Wilson).

*Behavior.*—Drop off cleanly; not particularly affected by cold, hot, wet or dry weather.

*Flower longevity.*—On bush in garden—4 or 5 days in July. Cut roses grown outdoors and kept at living-room temperatures—4 or 5 days in July.

*Reproductive organs*

Stamens: From few to average number; arranged regularly about pistils.

Filaments: Medium length; from 3 mm. to 9 mm. in length; most with anthers.

Anthers: Medium size; all open approximately at once. Color: upper side—margins near Cadmium Orange, Plate 8/2, page 8 (Wilson), with remainder near Indian Yellow, Plate 6/3, page 6 (Wilson); under side—margins near Cadmium Orange, Plate 8/2, page 8 (Wilson), with remainder near Indian Yellow, Plate 6/3, page 6 (Wilson).

Pollen: Moderate quantity. Color—near Saffron Yellow, Plate 7/2, page 7 (Wilson).

Pistils: Few; approximately 36 in number.

Styles: Moderately uneven; short; from 3 mm. to 8 mm. in length; thin; bunched. Color—near Scarlet, Plate 19/2, page 19 (Wilson).

Stigma: Color—near Maize Yellow, Plate 607/2, page 69 (Wilson).

Ovaries: Usually all enclosed in calyx.

Hips: From short to average length; globular; smooth; with few stipitate glands near attachment of peduncle; walls thick and fleshy. Color (mature)—near Salmon Orange, Plate II (Ridgway).

Sepals: Permanent; from short to medium length; somewhat curled and recurved. Color: inside—near Vetiver Green, Plate XLVII (Ridgway); outside—near Biscay Green, Plate XVII (Ridgway), sometimes overlaid with near Ocher Red, Plate XXVII (Ridgway).

Seeds: Average number; from 6 to 10 in number; usually medium size.

*Plant*

Foliage:

*Leaves.*—Compound of usually 5 to 7 leaflets; abundant; from medium size to large; leathery and semi-glossy.

*Leaflets.*—Shape—ovoid, with apex acute. Base—round. Margin—simply serrate.

*Color.*—Mature: upper surface—near Dark Dull Yellow-Green, Plate XXXII (Ridgway); under surface—near Light Grape Green, Plate XLI (Ridgway). Young: upper surface—near Deep Dull Yellow-Green, Plate XXXII (Ridgway); under surface—near Asphodel Green, Plate XLI (Ridgway), usually overlaid with near Vinaceous Brown, Plate XXXIX (Ridgway).

*Rachis (the supporting stem of the compound leaf).*—Average size. Upper side—grooved; with many stipitate glands on edges. Under side—smooth; with few prickles and stipitate glands.

*Stipules.*—From medium length to long; medium width; with medium length points turning out at an angle of less than 45°.

*Disease resistance.*—Better-than-average resistance to mildew, as compared with other varieties grown under comparable cultural conditions at Ontario, California.

Growth:

*Habit.*—Upright-spreading; much-branched.

*Growth.*—Vigorous.

*Canes.*—Heavy.

*Main stems.*—Color—near Rainette Green, Plate XXXI (Ridgway). Large prickles—several; from medium length to long; hooked downward; with medium length, narrow base; color—near Sayal Brown, Plate XXIX (Ridgway). Small prickles—none. Hairs—none.

*Branches.*—Color—near Courge Green, Plate XVII (Ridgway). Large prickles—several; from medium length to long; hooked slightly downward; with medium length, narrow base; color—near Orange Cinnamon, Plate XXIX (Ridgway). Small prickles—none. Hairs—none.

*New shoots.*—Color—between Fawn Color, Plate XL (Ridgway) and Buffy Brown, Plate XL (Ridgway). Large prickles—few; from short to medium length; hooked slightly downward; with medium length, narrow base; color—near Cameo Brown, Plate XXVIII (Ridgway). Small prickles—none. Hairs—none.

I claim:

A new and distinct variety of rose plant of the floribunda class, substantially as herein shown and described, characterized particularly as to novelty by its unique combination of a very vigorous, bushy, upright-spreading plant habit, attractive semi-glossy to glossy foliage of from medium to large size, semi-double flowers of from small to medium size borne in clusters of medium size, and a bright, relatively unfading flower color ranging from Cherry to Rose Red.

No references cited.